United States Patent [19]
Mathers et al.

[11] Patent Number: 5,096,862
[45] Date of Patent: Mar. 17, 1992

[54] TRANSPARENT CERAMIC COMPOSITE ARTICLE COMPRISING ALUMINUM OXIDE AND ALUMINUM MAGNESIUM OXYNITRIDE

[75] Inventors: James P. Mathers, Woodbury; Robert G. Frey, White Bear Lake, both of Minn.

[73] Assignee: Minnesota Mining and Manufacturing Company, St. Paul, Minn.

[21] Appl. No.: 565,057

[22] Filed: Aug. 9, 1990

[51] Int. Cl.$^5$ .................... C04B 35/58; C04B 35/20
[52] U.S. Cl. .................... 501/98; 501/96; 501/118; 501/153; 501/904; 501/125
[58] Field of Search ............ 501/96, 98, 127, 118, 501/120, 153, 904, 125; 423/630, 631, 635, 639

[56] References Cited

U.S. PATENT DOCUMENTS

| | | | |
|---|---|---|---|
| 3,026,210 | 3/1962 | Coble | 106/39 |
| 4,241,000 | 12/1980 | McCauley et al. | 264/65 |
| 4,481,300 | 11/1984 | Hartnett et al. | 501/98 |
| 4,520,116 | 5/1985 | Gentilman et al. | 501/98 |
| 4,686,070 | 8/1987 | Maguire et al. | 264/1.2 |
| 4,720,362 | 1/1988 | Gentilman et al. | 264/1.2 |

FOREIGN PATENT DOCUMENTS

| | | |
|---|---|---|
| 59-46439 | 9/1985 | Japan. |
| 60-191061 | 9/1985 | Japan. |

OTHER PUBLICATIONS

"Study on the Reductive Spinel-A New Formula Al-N-Al$_2$O$_3$ Instead of the Previous One Al$_2$O$_4$" *Bull. Chem. Soc. Jap.*, 32 (11), Nov. 1959, pp. 1264-1265.

"On the Formation of High Temperature Nonstoichiometric Spinels and Derivative Phases, In Several Oxide Systems Based on Alumina and in the System Aluminum Nitride Alumina," *Rev., Hautes, Temper. et Refract.*, Ch. 5, 1, 1964, pp. 58-95.

"The System Al-Mg-O-N", *J. Am. Ceram. Soc.*, 65, (5-6), 1982, pp. C-68-69.

"A Simple Model for Aluminum Oxynitride Spinels", *J. Am. Ceram. Soc.*, 61, (708), 1978, pp. 372-373.

"Phase Relationships in the System Mg-Al-O-N", Sun et al., *Chinese Science Bulletin*, vol. 35, No. 14, [Jul. 1990] pp. 1189-1192.

*Primary Examiner*—William R. Dixon, Jr.
*Assistant Examiner*—Paul Marcantoni
*Attorney, Agent, or Firm*—Gary L. Griswold; Walter N. Kirn; Lorraine R. Sherman

[57] ABSTRACT

This invention provides a transparent ceramic article comprising aluminum oxide and aluminum magnesium oxynitride. The ceramic article of the present invention is useful in applications where it is desirable to have an optically transparent ceramic including, for example, in orthodontic brackets, ferrules, and gas tight envelopes.

19 Claims, 3 Drawing Sheets

TRANSPARENT CERAMIC COMPOSITE ARTICLE COMPRISING ALUMINUM OXIDE AND ALUMINUM MAGNESIUM OXYNITRIDE

FIELD OF THE INVENTION

This invention relates to a transparent ceramic article comprising aluminum oxide and aluminum magnesium oxynitride. The ceramic article of the present invention is useful in applications where it is desirable to have a transparent ceramic including, for example, dental devices (e.g., orthodontic brackets), ferrules, gas tight envelopes (e.g , high pressure sodium vapor discharge lamps), radomes, and windows for infrared sensors, armor, chemical processing equipment, and high temperature ovens.

BACKGROUND ART

Transparent polycrystalline ceramics are known in the art. There are, however, two significant difficulties in the preparation of such ceramics: 1) randomly oriented polycrystalline anisotropic ceramics, which inherently have a different refractive index along at least two crystal axes, scatter light at each grain boundary and 2) ceramics comprising two or more phases having different refractive indices scatter light at each phase boundary. Second phases include pores which may be present in ceramics. Such pores contain gases which have a refractive index of about 1.0 whereas the refractive index of a ceramic is typically significantly greater than 1.0 (e.g., in the range of 1.4 to 2.8).

Polycrystalline aluminum oxide is used as an optically transparent ceramic in certain applications (e.g., high pressure sodium vapor discharge lamps). The transparency of polycrystalline alumina, however, is limited because of its anisotropic crystal structure. An alternative to alumina is gamma-aluminum oxynitride. Gamma-aluminum oxynitride, commonly referred to as "AlON", is an AlN-$Al_2O_3$ solid solution. In the early literature this material was sometimes referred to as "nitrogen stabilized cubic $Al_2O_3$." Gamma-aluminum oxynitride is more transparent than alumina because the former has a cubic crystal structure which is inherently isotropic whereas the latter has a non-cubic crystal which is inherently non-isotropic.

Synthesis of aluminum oxynitride was first reported by Yamaguchi et al. in "Study on the Reductive Spinel—A New Spinel Formula AlN-$Al_2O_3$. Instead of the Previous One $Al_3O_4$", Bull. Chem. Soc. Jap., 32, (11), Nov., 1959, pp. 1264–65, wherein alumina and graphite were reacted above 1650° C. in an unspecified atmosphere. The composition and structure of gamma-aluminum oxynitride were later described in more detail by Lejus in "On the Formation of High Temperature Nonstoichiometric Spinels and Derivative Phases, In Several Systems Based on Alumina and In The System Aluminum Nitride-Alumina", Rev. Hates Temper. et Refract., Ch. 5, 1, 1964, pp. 58-95. Lejus's preparation of aluminum oxynitride included reacting aluminum nitride and alumina.

U.S. Pat. No. 4,241,000 discloses a structural ceramic material comprising sintered single phase, polycrystalline, cubic aluminum oxynitride which displays isotropic optical, thermal, and electrical properties, an infrared cutoff at about 5.2 micrometers, and which shows no chemical or physical property change after heating to 1100° C. in an air atmosphere. The aluminum oxynitride ceramic was prepared by isostatically pressing a mixture of aluminum nitride and alumina powders, heating in nitrogen for 24 hours at 1200° C., and then sintering in nitrogen at 1975° C. for 1 hour.

Use of sintering aids, such as boron, yttrium, lanthanum compounds, or combinations thereof, to improve the optical transparency of sintered Alon is disclosed in U.S. Pat. Nos. 4,481,300, 4,520,116, 4,686,070, and 4,720,362 and in unexamined Japanese Patent No. SHO60-191061 published Sept. 28, 1985. The latter also describes an improvement in optical transparency by using aluminum nitride powder with a mean particle size diameter of less than 2 micrometers.

Weiss et al. in "The System Al—Mg—O—N", J. Am. Ceram. Soc., 65, (5-6), 1982, pp. C-68-69, reported that although an understanding of the phase relations and compositions of the Al—Mg—O—N system is still incomplete, gamma aluminum magnesium oxynitride may be described by the formula,

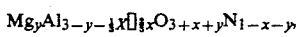

wherein the temperature-dependent solubility limits are $0 \leq x \leq 1$; $0 \leq y \leq 1$; and $x+y=1$. The authors did not disclose or suggest a transparent gamma-aluminum magnesium oxynitride, nor did they disclose a possible use of this ceramic material.

U S. Pat. No. 3,026,210 discloses the use of up to 0.5 weight percent MgO as a sintering aid in the preparation of transparent $Al_2O_3$. The presence of higher amounts of MgO resulted in a reduction in transparency due to the increased formation of a $MgAl_2O_4$ second phase.

The strength of a ceramic is inversely related to its grain size. The average grain size of the aforementioned transparent alumina and aluminum oxynitride-based ceramics is typically in the range of 25 to 200 micrometers. The relatively large grain size results from the long sintering times (i.e., 20 to 100 hours) and high sintering temperatures (i.e., 1600° to 2000° C.) needed to remove residual pores.

One way of limiting grain growth is to utilize a composite of two materials which are in equilibrium with each other at the sintering temperature. The presence of two different crystal types limits the volume in which the individual crystals (grains) can grow without impinging on each other. The difficulty with this approach of preparing a fine-grained ceramic is that rarely do two material have refractive indices similar enough to avoid scattering.

Alumina and aluminum oxynitride have refractive indices of 1.76 and 1.77, respectively. Even with this degree of index matching, significant scattering may occur which severely limits the transparency of the composite.

Although European Patent Application No. 0107571 discloses a composite comprising alumina and aluminum oxynitride, there was no suggestion that it was transparent.

SUMMARY OF THE INVENTION

Briefly, the present invention provides a transparent ceramic article comprising alumina ($Al_2O_3$) and aluminum magnesium oxynitride (AlMgON). Preferably, MgO is present in the aluminum magnesium oxynitride phase in the range of 0.25 to 2 weight percent, based on the total aluminum oxide-aluminum magnesium oxynitride composite composition. Preferably, the transparent ceramic article comprises in the range of 1 to 99 volume percent alumina and 99 to 1 volume percent aluminum magnesium oxynitride, based on the total volume of the transparent ceramic article. More preferably, the transparent ceramic article comprises in the range of 45 to 65 volume percent alumina and in the range of 55 to 35 volume percent aluminum magnesium oxynitride, based on the total volume of the transparent ceramic article.

Preferably, the transparent article according to the present invention is colorless.

Preferably, pores (voids), if present, in the ceramic article of the present invention have a diameter less than 1 micrometer. More preferably, the diameter of the pores is less than 0.3 micrometer.

Preferably, the transparent ceramic article of the present invention comprises less than 2 volume percent voids, based on the total volume of the transparent ceramic article (i.e., has a density greater than 98% of theoretical). More preferably, the density is greater than 99.5%. Even more preferably, it is greater than 99.8%, and most preferably it is 100.0%.

Preferably, the ceramic article of the present invention is prepared by mixing $Al_2O_3$ and AlN powders, at least one of MgO and $MgAl_2O_4$ powders, wherein the ratio of the powders is sufficient to provide the ceramic article of the present invention, and at least one organic binder, shaping the resulting mixture, heating the green shaped article to a temperature and for a time sufficient to burn out organic substituents, and then further heating the shaped article to a temperature and for a time sufficient to provide a sintered, transparent aluminum oxide-aluminum magnesium oxynitride composite ceramic.

The preferred starting materials are alumina, aluminum nitride, and magnesium oxide powders. Another preferred starting material which may be used as a source of alumina and magnesium oxide is $MgAl_2O_4$.

The oxynitride-based ceramic article of the present invention may be sintered in a hydrogen, a nitrogen, or an inert (e.g., argon, helium, etc.) atmosphere. The preferred sintering atmosphere is nitrogen.

In this application:
"ceramic" means an inorganic nonmetallic material, such as metal oxides, metal nitrides, and metal oxynitrides, consolidated by the action of heat;
"green" refers to an article which is unfired (i.e., not in its final ceramic form);
"sintering" means densification or consolidation of a powder compact during firing;
"grain" means an individual crystal which together with other grains make up a polycrystalline ceramic body;
"crystallite" means a crystal smaller than 10 micrometers in size;
"optical density", D, is defined according to the equation, $$D = \log \frac{I_o}{T},$$

wherein $I_o$ is the intensity of the incident ray of radiation in the visible range (i.e., having a wavelength in the range of 0.38 to 0.76 micrometer) and I is the intensity of the transmitted ray of radiation;
"transparent" means having a percent diffuse transmission value, T, of at least 35%, based on a flat, polished 1.25 mm thick body, wherein percent diffuse transmission is related to optical density according to the equation, $$D = \log \frac{1}{T};$$

"colorless" means substantially free of color, and preferably it means an absence of color (i.e., clear);
"AlON" means an aluminum oxynitride ceramic having a cubic spinel structure wherein the ceramic is an $Al_2O_3$—AlN solid solution (Our own experiments suggest AlON has a composition range given by the formula, $Al_{(2+x)}O_3N_x$, wherein X is in the range of 0.24 to 0.55.); having a cubic spinel structure wherein the ceramic is an $Al_2O_3$—MgO—AlN solid solution; and
"reaction sintering" means a heat-treatment in which powders react with each other and then sinter to form a dense, consolidated body.

Useful articles comprising the transparent ceramic of the present invention include, for example, dental devices, ferrules, and gas tight envelopes.

Several embodiments comprising the inventive transparent ceramic may preferably be bonded to a substrate during use. For example, dental devices may be bonded to a tooth, an optical fiber may be bonded to a ferrule, etc.

A preferred method of bonding a transparent ceramic article according to the present invention to a substrate comprises the step of curing a radiation curable resin which is in contact with a surface of a transparent ceramic article according to the present invention and a surface of a substrate, wherein the curable resin is exposed to electromagnetic radiation transmitted through the transparent ceramic article in an amount sufficient to cure the resin.

Preferably, the electromagnetic radiation has at least one wavelength in the range of 0.38 to 0.76 micrometer. More preferably, the electromagnetic radiation has at least one wavelength in the range of 0.40 to 0.70 micrometer. The preferred radiation curable resin is cured by exposure to electromagnetic radiation having at least one wavelength in the range of 0.38 to 0.76 micrometer. More preferably, the resin is cured by exposure to radiation having at least one wavelength in the visible range (i.e., in the range of 0.40 to 0.70 micrometer).

A transparent article consisting essentially of aluminum magnesium oxynitride is disclosed in assignee's copending patent application, U.S. Ser. No. 07/565,058, filed the same date as this application.

The art does not disclose or suggest a sintered transparent ceramic composite comprising $Al_2O_3$ and AlMgON.

BRIEF DESCRIPTION OF THE DRAWING

In the accompanying Drawing.

DETAILED DESCRIPTION OF PREFERRED EMBODIMENTS

Figure 1:
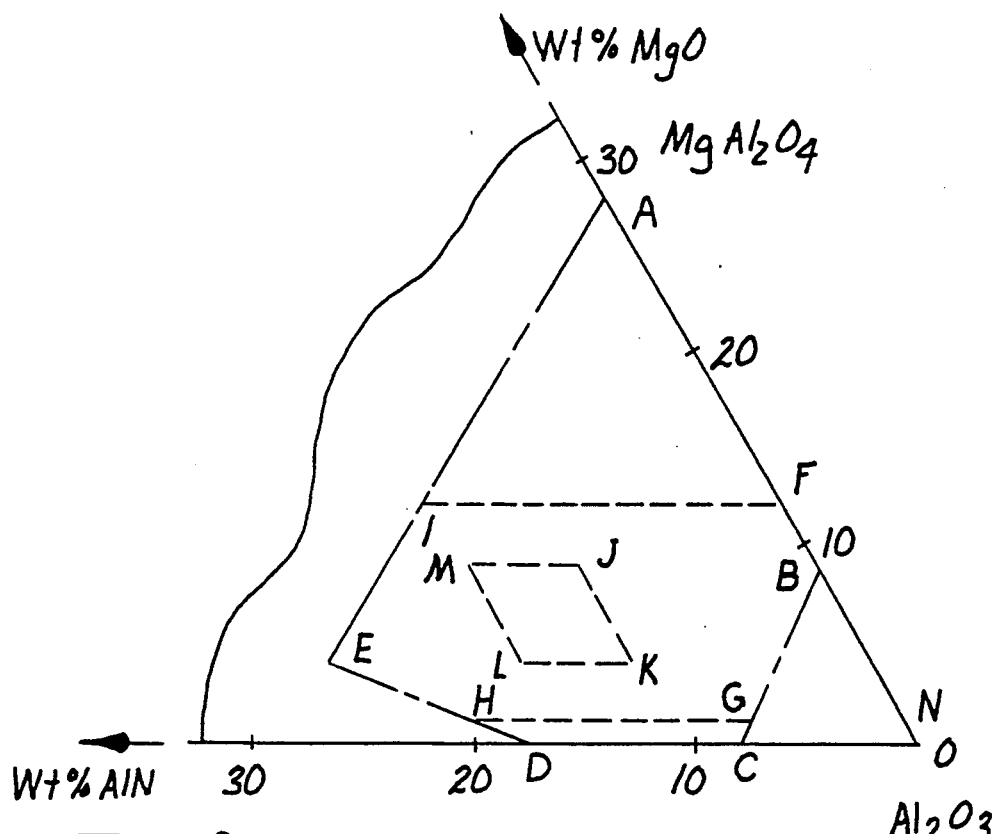
FIG. 1 represents a portion of an $Al_2O_3$—MgO—AlN phase diagram.

Referring to FIG. 1, which represents a portion of an $Al_2O_3$—MgO—AlN ternary phase diagram, the approximate solid solution range for MgO in AlON falls within the area or along the boundary defined by ABC-DEA. Transparent aluminum magnesium oxynitride-based compositions fall within the area or along the boundary defined by FBGHEIF. The composition of the most preferred transparent aluminum magnesium oxynitride-based ceramic comprising the composite ceramic of the present invention fall within the area or along the boundary defined by JKLMJ.

The composition of transparent ceramic composites according to the present invention are located in the two phase (i.e., $Al_2O_3$ and AlMgON) region of FIG. 1 defined by BCNB.

The ceramic article of the present invention can be prepared using commercially available raw materials. Preferably, the raw materials are oxide and nitride powders which comprise less than 100 parts per million transition metal (e.g., Fe, Ti, Co, Ni, Cr, and Zr) based on the total weight of the oxide and nitride powders. The presence of such impurities may cause aluminum oxynitride-based ceramics sintered in a nitrogen atmosphere to exhibit an undesirable gray to brown tint. It is preferable that the AlN powder have a low residual carbon content (i.e., less than 0.1 weight percent based on the weight of the AlN powder).

Preferably the raw materials are $Al_2O_3$ (available from, for example, Union Carbide Corp.; Indianapolis, Ind.), AlN, (Tokuyama Soda Co.; Tokyo, Japan), and MgO (Baikowski International; Charlotte, N.C.) powders. Another preferred starting material, $MgAl_2O_4$ (TAM Ceramics; Niagara Falls, N.Y.) powder may be used as a source of alumina and magnesium oxide.

Raw materials used to prepare the ceramic article of the present invention preferably have a particle size of 5 micrometers or less, more preferably in the range of 0.01 to 5 micrometers, and most preferably in the range of 0.1 to 2 micrometers. Raw materials comprising aggregates of weakly bonded crystallites, however, may also be useful provided the crystallites comprising the aggregates are within the preferred size range and the bonds between the crystallites are sufficiently weak such that the aggregates may be reduced to the preferred size. Size reduction of the aggregates may be accomplished by conventional techniques including, for example, ball-milling.

The surface area of a powder is inversely related to the crystallite size. Preferably, the oxide and nitride powders have a surface area in the range of 1 to 20 $m^2/g$. Powders with a surface area less than 1 $m^2/g$ tend to be difficult to reduce in size. Powders with a surface area greater than 20 $m^2/g$ tend to provide powder compacts with relatively high void volumes making it difficult to sufficiently eliminate pores during sintering.

The raw materials may be mixed by conventional techniques including, for example, ball-milling, attritor milling, vibratory-milling, high-shear mixing, and sonic dispersion. Useful processes include those capable of breaking down any aggregates, if present, to within the preferred size range. Care should be taken in mixing the raw materials to minimize contamination from milling media, mill jar, mixing blades, etc. Contaminants which may be detrimental to the preparation of the ceramic article of the present invention include, for example, transition metals or compounds thereof.

AlN powders and mixtures thereof should be protected from moisture pickup prior to heating or sintering. AlN may react with water to form ammonia and aluminum hydroxide. The loss of nitrogen in the form of ammonia gas may result in a final ceramic composition deficient in nitrogen.

Conventional organic binders, lubricants, etc., known to aid in the formation of a green article may be added to the powders preferably in an amount up to 50 volume percent. Organic binders useful in preparing the green article of the present invention include, for example, polyethylene glycol. Organic lubricants include, for example, stearic acid.

In a preferred method, a ball mill is charged with the appropriate oxide and nitride powders, organic binder, mill media, and an organic solvent, such as, for example, an alcohol (e.g., ethanol or methanol), ketone (e.g., acetone), trichloroethane, toluene, xylene, hexane, the like, or compatible combinations thereof. The preferred organic solvent is ethanol. In a more preferred method, the raw materials are ball milled dry (i.e., no solvent is added to the ball mill).

The wet or dry charge is milled for a time sufficient to thoroughly mix the raw materials and to adequately reduce the size of the particles/aggregates comprising the powder. Preferably, the milling time is not long enough to allow impurities from the mill media, mill jar, mixing blades, etc. to contaminate the slurry. Preferably, the charge is milled for a time period in the range of 0.5 to 24 hours. More preferably, milling time is about 6 hours. After milling, the solvent, if present, may be evaporated by heating.

Conforming methods may be used to prepare a shaped, green article of the present invention including, for example, dry-pressing, slip-casting, tape casting, and extrusion.

If a green article is shaped by dry-pressing, a powder cake, which typically forms when the solvent is evaporated, may be reduced in size by any means known in the art, including, for example, by gently crushing it with a mortar and pestle and then screening, to provide agglomerates in a size range suitable for dry-pressing (i.e., less than 250 micrometers).

Preferably, the green article of the present invention is heated to a temperature and for a time sufficient to burn out organic substituents, if present, in the powder mixture. More preferably, the green article is slowly heated to a temperature in the range of 300° to 1000° C. for a time sufficient to burn out organic substituents, if present, in the powder mixture. The preferred heating rate is dependent on the atmosphere in which the article is heated and the amount and type of organic substituents which may be present. Preferably, the heating rate is slow enough to minimize or prevent cracking, bloating, or distortion of the article during the removal of organic substituents Removal of organic substituents at up to 600° C. may take place in an air, nitrogen, or inert atmosphere or in a vacuum. Removal of organic substituents at temperatures above 600° C. preferably takes place in a nitrogen or inert atmosphere to prevent oxidation of the AlN. The selection of the burn-out atmosphere and temperature preferably is such that the amount of any residual carbon from organic substituents is not sufficient to cause the sintered article to be substantially discolored.

An important factor in determining the transparency of a sintered article is the number of pores. In general, the fewer the pores, the higher the transparency. Pores are formed during sintering when voids present in an unfired article, which contain furnace gas, are sealed off during the sintering process. As the sintering process progresses pores are removed via diffusion. To minimize the number of pores in a fired pure oxide ceramic (e.g., alumina), it is usually necessary to fire either in a vacuum or hydrogen atmosphere. Although the diffusion rate of hydrogen through a ceramic oxide is significantly faster than the rate for any other gas, its flammability raises safety concerns. A vacuum furnace on the other hand is significantly more expensive than a furnace with a conventional firing atmosphere (e.g., nitrogen). Unlike pure oxide ceramics the transparent aluminum oxynitride-based ceramic composite of the present invention may also be sintered in a nitrogen or inert (e.g., He, Ar, etc.) atmosphere.

The preferred atmosphere for sintering the article of the present invention is nitrogen. Sintering in a nitrogen atmosphere tends to suppress volatilization of the nitrogen contained in an aluminum magnesium oxynitride ceramic or precursor thereof.

Volatilization of aluminum nitride and aluminum magnesium oxynitride may be further suppressed by packing the green article in a compatible powder or sand such as, for example, aluminum nitride, aluminum oxynitride, alumina, or combinations thereof. Preferably the powder or sand comprises 5% by weight of aluminum nitride (average particle size of 0.7 micrometer) and 95% by weight of alumina (average particle size of 300–420 micrometers), or aluminum oxynitride (average particle size of 300 to 420 micrometers). Such sands or powders preferably have a low transition metal content (i.e., less than 100 parts per million by weight).

The preferred sintering temperature is in the range of 1600° to 1900° C., and more preferably in the range of 1800° to 1900° C. Preferably, the sintering time is in the range of 2 to 20 hours, and more preferably in the range of 5 to 15 hours.

In a more preferred process, the article is heated to and held at a temperature in the range of 1700° to 1800° C. for 0.5 to 1 hour prior to heating to a temperature in the range of 1800° to 1900° C.

The transparent ceramic composite of the present invention is useful in applications where it is desirable to have a transparent material including, for example, dental devices (e.g., orthodontic brackets) ferrules (e.g., the alignment pin of a fiber optic connector), and gas tight envelopes (e.g., high pressure sodium vapor discharge lamps). Other utilities of the composite ceramic of the present invention include radomes, and windows for infrared sensors, armor, chemical processing equipment, and high temperature ovens.

Figure 4:
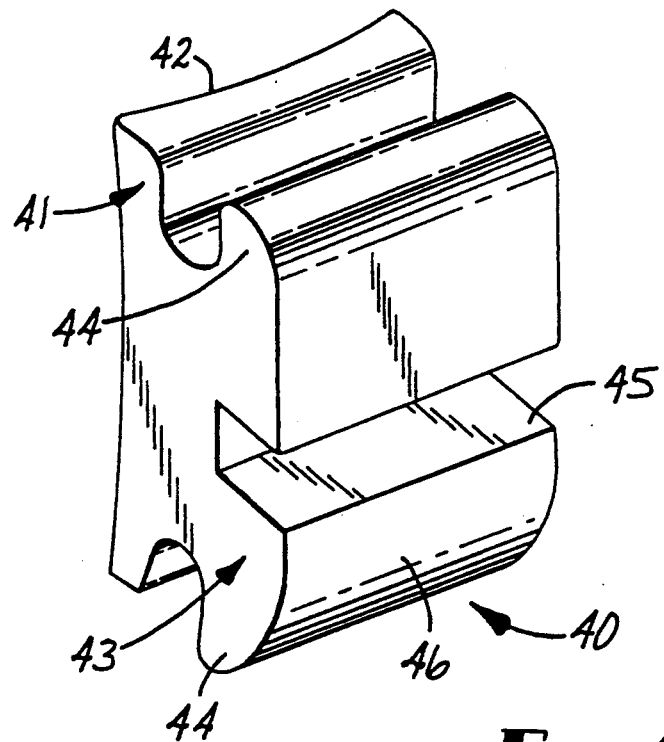
FIG. 4 illustrates a preferred orthodontic device according to the present invention.

A preferred dental device is orthodontic bracket 40 shown in FIG. 4. The bracket has base 41 suitable for either direct bonding to a tooth, or attachment to any kind of mounting fixture. Tooth-facing surface 42 of base 41 is preferably conventionally concavely curved about both a mesiodistal axis and an apical axis to match the natural convexity of the tooth's labial surface or lingual surface to allow direct attachment to at least a portion of the labial or lingual surface. Other curvatures can be used to accommodate labial or lingual bracket positioning.

Bracket body 43 extends from base 41 to define bracket tie wings 44 for ligature anchorage, and mesiodistally oriented arch-wire slot 45 extending from outer body surface 46 into the bracket body. Tie wings 44 may be in either a single or twin configuration (single configuration shown). Angulation of base 41 and arch-wire slot 45 may vary to take advantage of torquing and bending of the arch-wire to create tooth movement forces in the desired direction.

In another preferred embodiment, toothfacing surface 42 of base 41 is shaped to allow for attachment of a metal band to the orthodontic bracket, wherein the metal band encircles the perimeter of the tooth.

The term "orthodontic device" is herein used in a broad sense to include any device intended for mounting on a tooth, and used to transmit to the tooth corrective force from an arch-wire, spring, elastic, or other activatable force-applying component. Similarly, the term "arch-wire slot" is used broadly to designate any bracket structure which receives or couples with the force applying component. The term is thus intended to include such equivalent structures as a buccal tube which receives a facebow or similar device.

It is within the scope of this invention to include other useful orthodontic bracket configurations known in the art including those disclosed in U.S. Pat. Nos. 4,784,606 and 4,915,625, and assignee's co-pending patent application, U.S. Ser. No. 07/248,297, filed Sept. 21, 1988.

In a preferred method, the position of a tooth may be changed by the step of providing an orthodontic bracket, having a toothfacing surface and an archwire receiving slot therein, comprising the transparent aluminum oxynitride-based ceramic of the present invention; and securing the orthodontic bracket to a tooth and connecting an orthodontic archwire adjacent to the archwire receiving slot, wherein the orthodontic archwire provides sufficient force to move the tooth to a desired position over a period of time.

The orthodontic bracket according to the present invention may be secured to the tooth by techniques known in the art including, for example, banding or bonding. In a preferred method, the orthodontic bracket is secured to the tooth with a light curable adhesive resin, wherein the light curable resin is exposed to electromagnetic radiation, and wherein the electromagnetic radiation is transmitted through the orthodontic bracket in an amount sufficient to cure the resin. In a more preferred method, the surface of the tooth is cleaned with pumice, rinsed with water, dried, etched with 37% phosphoric acid (preferably for about 15 seconds), rinsed with water (preferably for at least 45 seconds), air dried, and coated with a dental primer (i.e., applying an uncured dental primer and then curing it), prior to putting the light curable resin in contact with the tooth surface.

Light curable resins which are useful for bonding the orthodontic bracket to a tooth are commercially available, and include, for example, TRANSBOND TM Light Cured Orthodontic Adhesive (3M Unitek Corp. of Monrovia, Calif.). Useful dental primers are commercially available, and include, for example, TRANSBOND TM Light Cured Orthodontic Primer (3M Unitek Corp.).

The fiber connector according to the present invention has a ferrule comprising the transparent ceramic of the present invention.

Figure 5:
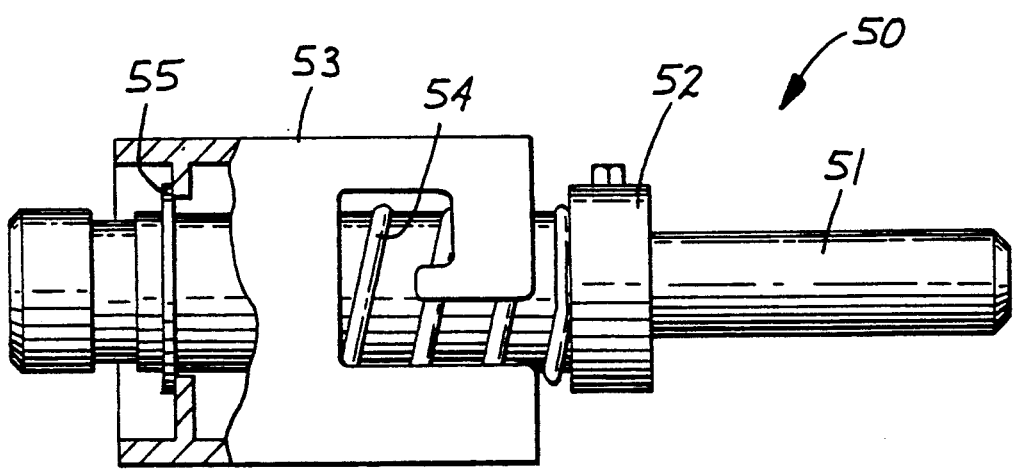
FIG. 5 illustrates a preferred fiber connector according to the present invention.

Preferred fiber connector 50, is shown in FIG. 5. Fiber connector 50 has ferrule 51 mounted inside backbone 52, housed in bayonet cap 53, wherein pressure is applied to bayonet cap 53 by spring 54, and wherein spring 54 is held by clip 55.

It is also within the scope of this invention to include other useful fiber connector configurations including, for example, those disclosed in U.S. Pat. Nos. 4,487,474 or 4,842,363.

A fiber comprised of glass (e.g., silica), plastic (e.g., polymethylmethacrylate), or the like, may be connected to a ferrule according to the present invention by techniques known in the art, including, for example, bonding with heat curable epoxy. Preferably, the fiber is bonded to the ferrule by a radiation curable resin, wherein the curable resin is exposed to electromagnetic radiation, and wherein the electromagnetic radiation is transmitted through the ferrule in an amount sufficient to cure the resin. The preferred radiation curable resin is a light curable resin. Light curable resins which are useful for bonding a fiber to the ferrule are commercially available, and include, for example, TRANSBOND TM Light Cure Orthodontic Adhesive (3M UNITEK Corp.), and SILUX TM Enamel Bond Resin (3M).

Objects and advantages of this invention are further illustrated by the following examples, but the particular materials and amounts thereof recited in these examples, as well as other conditions and details, should not be construed to unduly limit this invention. All parts and percentages given in the examples are by weight unless otherwise indicated.

All samples prepared in the Examples, unless specifically designated "Comparative", exhibit transparency as defined above.

EXAMPLE 1

Figure 2:
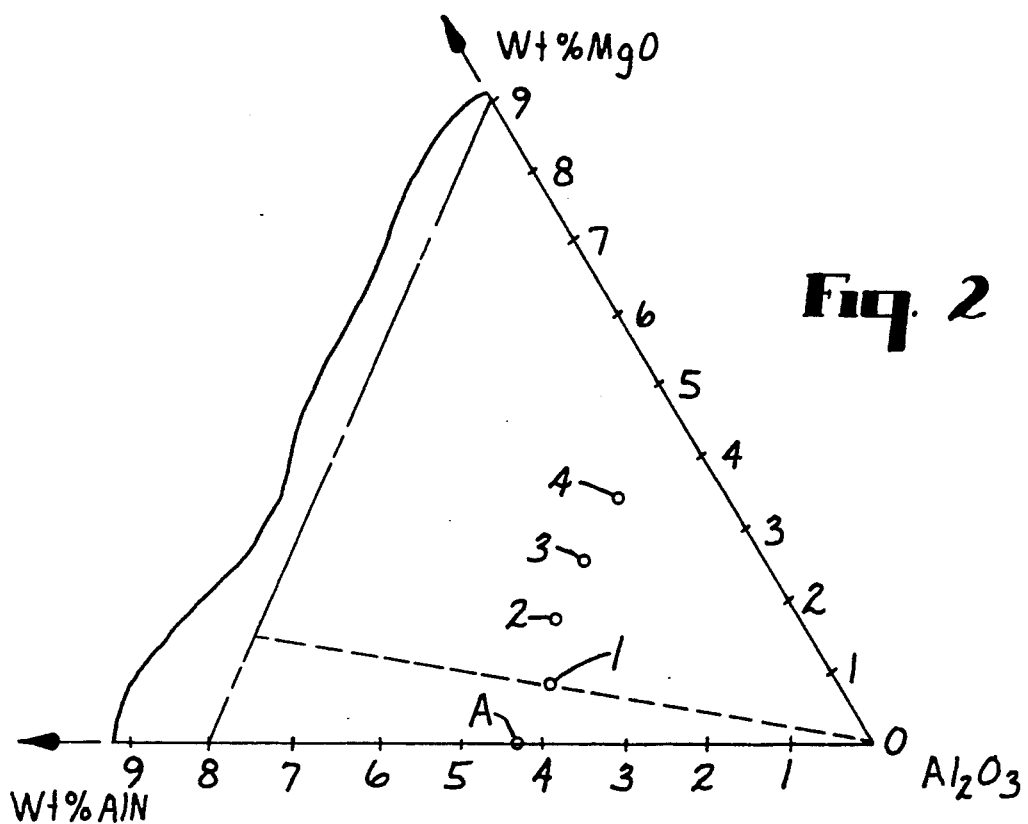
FIG. 2 illustrates the approximate compositions of Samples 1, 2, 3, and 4 and Comparative A of Example 1 within an $Al_2O_3$—MgO—AlN phase diagram.

Four samples of various compositions as disclosed in TABLE 1 below were prepared using the procedures described below. The approximate compositions of Samples 1, 2, 3, and 4 and Comparative A within the $Al_2O_3$—MgO—AlN phase diagram, are illustrated in FIG. 2. A 1.3 liter porcelain mill jar (ROLEX TM Size 00; Norton Co.; Akron, Ohio) was charged with $MgAl_2O_4$ (CERNEL TM 1; TAM Ceramics; Niagara Falls, N.Y.), AlN (Grade F; Tokuyama Soda Corp.; Tokyo, Japan), and $Al_2O_3$ (Linde TM C; Union Carbide Corp.; Indianapolis, Ind.) powders to provide a 60 gram batch. Three grams of polyethylene glycol (molecular weight of about 200), 166 grams of ethanol, and 1250 grams of high-alumina media (BURUNDUM TM rods, 6 mm long; Norton Co.) were also added to the jar. The contents of the jar were ball-milled for 6 hours at a speed of 60 rpm.

TABLE 1

| Sample | Composition MgO | AlN | $Al_2O_3$ | Thickness of pressed disc, mm | Thickness of polished disc, mm | Percent diffuse transmission, T |
|---|---|---|---|---|---|---|
| Comparative A | 0.0 | 4.3 | 95.7 | 2 | 1.4 | 48 |
| 1 | 0.9 | 3.4 | 95.7 | 2 | 1.4 | 68 |
| 2 | 1.7 | 3.0 | 95.3 | 2 | 1.4 | 50 |
| 3 | 2.5 | 2.2 | 95.3 | 2 | 1.4 | 37 |
| 4 | 3.4 | 1.3 | 95.3 | 2 | 1.4 | 20 |

After milling the resulting slurry was placed in a glass beaker and heated on a hot plate with stirring at 40° C. for a time sufficient to evaporate the ethanol. The dried slurry was then gently broken up with a mortar and pestle and passed through a 60 mesh sieve (U.S. Standard Series; Murdock, Inc.; Arlington Heights, Ill.).

About 0.5 grams of the minus 60 mesh powder was pressed into a disc 13 mm in diameter and about 2 mm thick at 140 MPa using a laboratory press (Carver Laboratory Press; Sterling, Inc.; Menomonie Falls, Wisc.).

Organic substituents were burned out of the disc by heating in a conventional furnace according to the following schedule:
20°→600° C. at 3° C./minute
600° C. hold for 0.5 hours
600°→20° C. at 10° C./minute.

The disc was then reaction-sintered in a boron nitride crucible (Grade HBN; Union Carbide Corp.; Cleveland, Ohio). The disc was surrounded by a sand/powder mixture comprising 90 percent coarse alumina sand (T-64 TM Tabular Alumina; ALCOA; Bauxite, Ark.) and 10 percent aluminum nitride powder (Grade F; Tokuyama Soda Co.; Tokyo, Japan). The disc was heated in a nitrogen atmosphere using a graphite element resistance furnace according to the following schedule:
20°→1000° C. in 15 minutes
1000°→1850° C. at 25° C./minute
1850° C. hold for 5 hours
1850°→20° C. in 1.5 hours.

The flat surfaces of the disc were ground using a conventional 15 micrometer metal bonded diamond abrasive disc to provide a thickness of 1.4+0.05 millimeters. The ground surfaces were polished with 1 micrometer alumina followed by a final polishing with 0.3 micrometer alumina.

A Model TR 927 Densitometer (Macbeth; Newburgh, N.Y.) was used to measure the "optical density", D, of each disc. The diffuse optical density values were converted into percent transmission values, T, using the equation, $$D = \log \frac{1}{T},$$

and are listed in TABLE 1.

It is known in the art that MgO has a low solubility in $Al_2O_3$. Weiss et al., *J. Am. Cer. Soc.*, 65, (5–6), 1982, pp. C-68-69, indicate that the MgO present in an AlON formulation is incorporated into the AlON structure rather than as a separate MgO phase. Although not wanting to be bound by theory or speculation, it is believed that Samples 1, 2, 3, and 4 comprise an $Al_2O_3$ phase and an AlMgON phase.

Sample 1, which contained 0.9 percent MgO, had the highest percent diffuse transmission (68%). The location of the composition of Sample 1 in regard to the $Al_2O_3$—MgO—AlN phase diagram is shown in FIG. 2 as Point 1. A tie line passing through Point 1 intersects the phase boundary for AlMgON.

Based on the phase diagram of FIG. 2, the AlMgON phase of Sample 1 should contain about 1.6% MgO. Although the amount of AlMgON present in the composites along the tie line passing through Point 1 will change, the percent MgO comprising the AlMgON phase will be constant. The constant composition of the $Al_2O_3$ and AlMgON phases comprising the composites along the tie line passing through Point 1 mean that the index of refraction match for all composites along the tie line will be the same.

The data in TABLE 1 show the percent diffuse transmission of an $Al_2O_3$—AlMgON composite increased as a function of the MgO content up to 0.9 percent based on the total weight of the $Al_2O_3$—AlMgON composite. Above 0.9 percent MgO the percent diffuse transmission decreased.

Although not wanting to be bound by theory it is believed that the amount of MgO present in the AlMgON phase affects its refractive index. The transparency of the composite improves as the refractive index of the AlMgON phase approaches that of the $Al_2O_3$ phase. The AlMgON composition which most closely matches the refractive index of $Al_2O_3$ has a composition of or near that present in Sample 1.

The optical clarity of the samples corresponded well to the percent diffuse transmission values (i.e., high transmission values mean high clarity). For example, a printed page of text (i.e., black type on white paper) placed under Sample 1 was noticeably clearer than when placed under Samples 2, 3, or 4 or Comparative A.

EXAMPLE 2

Figure 3:
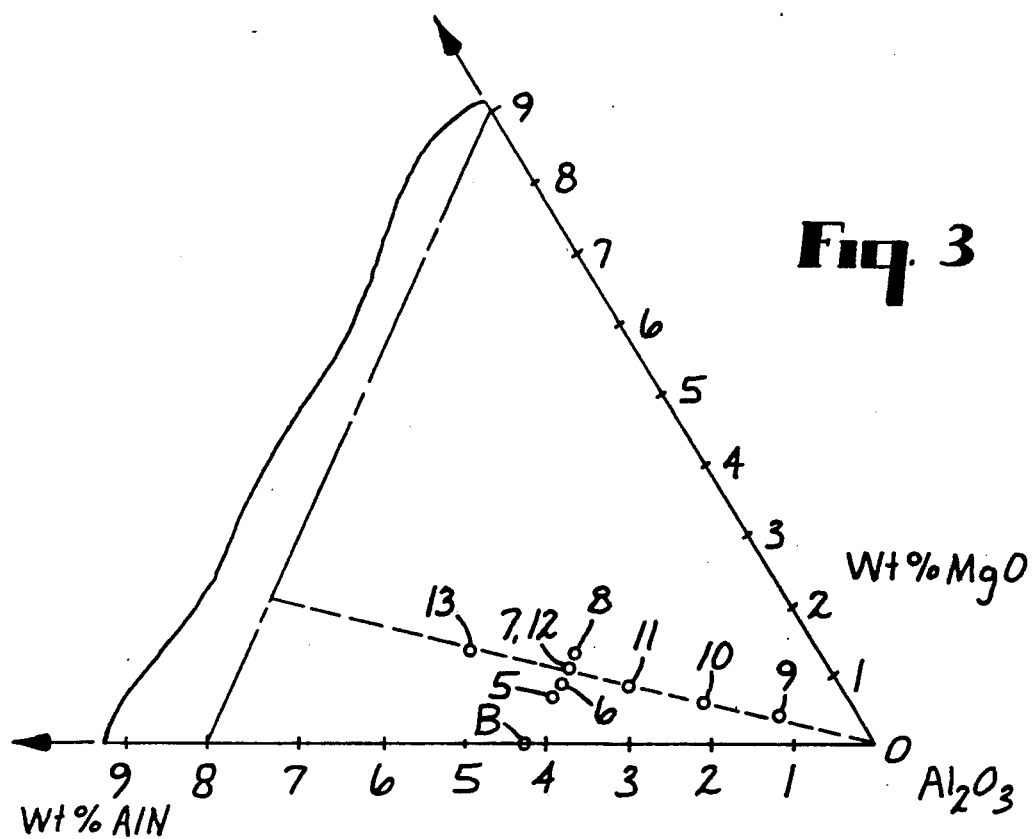
FIG. 3 illustrates the approximate compositions of Samples 5, 6, 7, and 8, and Comparative B of Example 2 and of Samples 9, 10, 11, 12, and 13, of Example 3 within an $Al_2O_3$—MgO—AlN phase diagram.

Four samples comprising 0.7 to 1.3 percent MgO, as disclosed in TABLE 2 below, were prepared using the procedures below. The approximate compositions of Samples 5, 6, 7, and 8 and Comparative B within a $Al_2O_3$—MgO—AlN phase diagram, are illustrated in FIG. 3. A one-liter high-density polyethylene mill jar (Nalge Co.; Rochester, N.Y.) was charged with $Al_2O_3$, AlN, and $MgAl_2O_4$ powders to provide a 60 gram batch. Twelve hundred grams of high-alumina media and three grams of polyethylene glycol (molecular weight of about 200) were also added to the jar. The contents of the jar were ball-milled for 6 hours at a speed of 96 rpm.

TABLE 2

| Sample | Composition | | | Thickness of pressed disc, mm | Thickness of polished disc, mm | Percent diffuse transmission, T |
| --- | --- | --- | --- | --- | --- | --- |
| | MgO | AlN | $Al_2O_3$ | | | |
| Comparative B | 0.0 | 4.3 | 95.7 | 4 | 2.8 | 28 |
| 5 | 0.7 | 3.6 | 95.7 | 4 | 2.8 | 47 |
| 6 | 0.9 | 3.4 | 95.7 | 4 | 2.8 | 51 |
| 7 | 1.1 | 3.2 | 95.7 | 4 | 2.8 | 55 |
| 8 | 1.3 | 3.0 | 95.7 | 4 | 2.8 | 46 |

After milling, the resulting powder was passed through a 60 mesh sieve as described in Example 1. One gram of the screened powder was pressed as described in Example 1 into a disc 13 mm in diameter and about 4 mm thick.

Organic substituents were burned out of the sample as described in Example 1 except the following heating schedule was used:
20°→600° C. at 3° C./minute
600° C. hold for 0.5 hours
600°→20° C. at 10° C./minute.

The disc was then reaction-sintered as described in Example 1 except the discs were surrounded by 95% alumina (prepared as described below) and 5% AlN powder and the heating schedule was as follows:
20°→1000° C. in 15 minutes
1000°→1700° C. at 25° C./minute
1700° C. hold for 1 hour
1700°→1850° C. at 25° C./minute
1850° C. hold for 10 hours
1850°→20° C. in 1.5 hours.

The sintered samples of Example 2 were all colorless.

The alumina sand used in the sintering step was prepared as follows. One hundred grams of synthetic boehmite (Dispersible Alumina; Chattem Chemicals; Chattanooga, Tenn.) was slowly added to 406.6 grams of distilled water heated to about 90° C., while stirring with a high shear mixer (Series 2000 Dispersator; Premier Mill Corp.; New York, N.Y.). The addition of the boehmite caused the temperature of the water to drop to about 80° C.

After stirring for 5 minutes with the high shear mixer, 4.5 grams of nitric acid was added slowly to the sol taking care to minimize foaming. The acidified sol was held at a temperature of about 80° C. and stirred for an additional 15 minutes.

The sol was then placed in a 3.8 liter (1 gallon), glass jar, covered, and heated for about 24 hours at about 90° C. The solid content of the sol was about 15 percent.

One thousand grams of the sol prepared as just described was placed in a 3.8 liter (1 gallon) polyethylene jar. Forty grams of a 25 percent $Al(NO_3)_3 \cdot 9H_2O$ aqueous solution was added to the sol while stirring by hand. The sol was then transferred to glass trays. Within about 15 minutes after the stirring was completed the sol behaved as a thixotropic gel. The gel was dried in the trays over night in ambient air. The gel was then heated in a convection oven at about 90° C. for about 24 hours.

The dried gel was crushed with a mortar and pestle and then screened to $-14+45$ mesh. The screened, dried gel was sintered in a conventional oven in air according to the following heating schedule:
25°→1200° C. at 9.8° C./minute
1200° C. hold for 1 hour
1200°→25° C. in 2 hours.

Each disc was ground and polished as described in Example 1, except the final thickness was $2.8 \pm 0.1$ mm. The percent diffuse transmission of each disc was determined as described in Example 1. The results are provided in TABLE 2.

The percent diffuse transmission increased as a function of MgO content up to 1.1 percent MgO. The diffuse transmission of the sample without MgO, Comparative B, was 28 percent, whereas the sample comprising 1.1 percent MgO, Sample 7, was 55 percent. The percent diffuse transmission decreased with the addition of more than 1.1 percent MgO. The percent diffuse transmission was 46 percent for the sample comprising 1.3 percent MgO, Sample 8.

EXAMPLE 3

Samples of Example 3, having the formulations provided in TABLE 3 below, were prepared as described in Example 2. The approximate compositions of Samples 9, 10, 11, 12, and 13 within an $Al_2O_3$—MgO—AlN phase diagram are illustrated in FIG. 3.

TABLE 3

| Sample | Composition | | | Thickness of pressed disc, mm | Thickness of polished disc, mm | Percent diffuse transmission, T |
| --- | --- | --- | --- | --- | --- | --- |
| | MgO | AlN | $Al_2O_3$ | | | |
| 9 | 0.4 | 1.1 | 98.5 | 4 | 2.8 | 28 |
| 10 | 0.6 | 1.8 | 97.6 | 4 | 2.8 | 35 |
| 11 | 0.9 | 2.5 | 96.6 | 4 | 2.8 | 59 |
| 12 | 1.1 | 3.2 | 95.7 | 4 | 2.8 | 51 |
| 13 | 1.3 | 4.4 | 94.3 | 4 | 2.8 | 20 |

The sintered samples were colorless with the exception of Sample 9 which was slightly gray.

The samples of this Example were ground and polished as described in Example 1 to a thickness of 2.8±0.1 mm. The percent diffuse transmission of each disc was determined as described in Example 1. The results are provided in TABLE 3.

Sample 11 had the highest percent diffuse transmission value, 59%. The percent diffuse transmission of Sample 7 of Example 2 and Sample 12 of Example 3, which both had the same composition and were prepared in the same manner, were comparable. The percent diffuse transmission for the former was 55%, whereas the value for the latter was 51%.

Two methods were used to determine the actual volume fraction of $Al_2O_3$ and AlMgON present in each sample for Example 3. In one method, the nitrogen content of each sample was determined using a TC-436 TM Nitrogen/Oxygen Analyzer (LECO Corp; St. Joseph, Mich.). The volume fraction of each phase was calculated from the measured nitrogen content based on the amount of nitrogen present in the AlMgON phase. The composition of the AlMgON phase contained in a sample can be determined from the $Al_2O_3$—MgO—AlN phase diagram shown in FIG. 2. The nitrogen content of the AlMgON phase at the intersection of a tie line passing through the formulations of Example 3 and the AlMgON phase boundary was estimated to be 2.2 percent. The results are provided in TABLE 4, below.

TABLE 4

| Sample | Percent nitrogen expected | Percent nitrogen detected | Volume Fraction based on the amount of nitrogen detected | |
|---|---|---|---|---|
| | | | $Al_2O_3$ | AlMgON |
| 9 | 0.32 | 0.33 | 0.85 | 0.15 |
| 10 | 0.60 | 0.54 | 0.71 | 0.29 |
| 11 | 0.81 | 0.75 | 0.62 | 0.38 |
| 12 | 1.01 | 0.96 | 0.52 | 0.48 |
| 13 | 1.25 | 1.31 | 0.41 | 0.59 |

The volume fraction of AlMgON ranged from 0.15 (Sample 9) to 0.59 (Sample 13).

In the second method, the volume fraction of the $Al_2O_3$ and AlMgON phases present in each sample were determined by conventional x-ray diffraction techniques. The weight percent $Al_2O_3$ and AlMgON were determined based on the diffraction patterns for $Al_2O_3$ and AlON. The similarity of the diffraction patterns for AlMgON and AlON is discussed in assignee's copending patent application, U.S. Ser. No. 07/565,058, filed the same date as this application, which is incorporated herein by reference.

It is known to one skilled in the art that the solubility of MgO in $Al_2O_3$ is low. For the determination of the volume fraction of the $Al_2O_3$ and AlMgON phases present in Samples 9, 10, 11, 12, and 13 it was assumed that all the magnesium oxide was in solid solution with the AlON and that both the $Al_2O_3$ and AlMgON phases diffract x-rays with equal intensity. The results are provided in TABLE 5, below.

TABLE 5

| Sample | X-ray diffraction, relative intensity | | Volume fraction based on relative x-ray intensity | |
|---|---|---|---|---|
| | $Al_2O_3$ | AlMgON | $Al_2O_3$ | AlMgON |
| 9 | 100 | 21 | 0.83 | 0.17 |
| 10 | 100 | 38 | 0.72 | 0.28 |
| 11 | 100 | 60 | 0.62 | 0.38 |
| 12 | 100 | 73 | 0.58 | 0.42 |
| 13 | 70 | 100 | 0.41 | 0.59 |

Both of the methods described above for determining the volume fraction of AlMgON and $Al_2O_3$ present in the samples of this example provided comparable results.

Sample 11 was bonded to a glass microscope slide using a light curable resin (commercially available under the trade designation "SILUX ENAMEL BOND RESIN" from 3M Company of St. Paul, Minn.) according to the following procedure.

A piece of black electrical tape (about 5 cm by about 2 cm) having a 0.63 cm diameter hole was placed onto one flat surface of the Sample 11 disc. One drop of the light curable resin was placed on a flat surface of the glass microscope slide. The flat surface of the disc opposite the electrical tape was gently pressed into the light curable resin.

The light curable resin was cured using a hand held curing unit (commercially available under the trade designation "VISILUX 2" from 3M Company of St. Paul, Minn.). The output of the light source was directed through the circular hole in the electrical tape. The resin was irradiated through the disc for about 10 seconds, which was sufficient to cure the resin.

EXAMPLE 4

In Example 4 the grain size and strength of an $Al_2O_3$—AlMgON composite ceramic (Sample 14) and single phase AlMgON ceramic (Comparative C) were compared. Fifteen discs of each sample were prepared to provide enough specimens for strength testing. Sample 14 was prepared in the same manner as Sample 11 in Example 3, except the thickness of the pressed disc was about 3 mm.

Comparative C was prepared in the following manner. A one liter high density polyethylene mill jar was charged with $MgAl_2O_4$, AlN, and $Al_2O_3$ powders to provide a 125 gram batch, 1200 grams of high-alumina media, 166 grams of ethanol, and 6.25 grams of polyethylene glycol (molecular weight of about 200). The jar was rotated at 96 rpm for about 12 hours. The slurry was dried, then screened and pressed in the same manner as Sample 14.

Organic substituents were burned out of the green comparative discs by heating according to the following schedule:
20°→600° C. in 15 minutes
600° C. hold for 0.5 hours
600°→20° C. at 10° C./minute.

The comparative discs were then reaction-sintered in a manner similar to Sample 14, except they were surrounded by a sand/powder mixture comprising 90 percent AlON sand (+40+50 mesh; prepared as described in U.S. Pat. No. 4,788,167) and 10 percent aluminum nitride powder and they were then heated according to the following schedule:
20° to 1000° C. in 15 minutes
1000°→1800° C. at 25° C./minute
1800° C. hold for 0.5 hours
1800°→1975° C. at 25° C./minute 1975° C. hold for 5 hours
1975°→20° C. in 2 hours.

The flat surfaces of one Sample 14 disc and one Comparative C disc were ground and polished as described in Example 1. The polished discs were then heat-etched in a furnace having a nitrogen atmosphere according to the following heating schedule:

25°→1000° C. in 20 minutes
1000°→1750° C. at 25° C./minute
1750° C. hold for 0.5 hours
1750°→25° C. in 1.5 hours.

The grain size associated with each microstructure was determined by the line intercept method described by Mendelson in "Average Grain Size in Polycrystalline Ceramics", *J. Am. Cer. Soc.*, 52, (8), 1969, pp. 443-46. The average grain sizes as determined by this method are given in TABLE 6, below.

TABLE 6

| Example | Composition | | | Average grain size, micrometers | Diametral tensile strength, MPa |
| --- | --- | --- | --- | --- | --- |
| | MgO | AlN | $Al_2O_3$ | | |
| Comparative C | 5.0 | 12.1 | 82.9 | 156 | 121 |
| Sample 14 | 0.9 | 2.5 | 96.6 | 3.9 | 324 |

The average grain size of the $Al_2O_3$—AlMgON ceramic composite was significantly finer than the average grain size of the AlMgON ceramic.

The diametral tensile strength of Sample 14 and Comparative C were determined using the procedures described by Rudnick et al. in "An Analysis of the Diametral-Comparison Test," *Mater. Res. Std.*, 3, (4), 1963, pp. 283-89. The loading surfaces of the test machine were padded with 0.25 mm thick brass plates. The results provided in TABLE 6 represent an average of 13 to 14 discs.

The data of TABLE 6 show the diametral tensile strength of the $Al_2O_3$—AlMgON ceramic composite was significantly higher than the diametral tensile strength of the AlMgON ceramic.

EXAMPLE 5

The sample of this example, Sample 15, was prepared in the same manner as Sample 11 of Example 3, except the disc was reaction-sintered according the following heating schedule:

20°→1000° C. at 65° C./minute
1000°→1700° C. at 25° C./minute
1700° C. hold for 1 hour
1700°→1850° C. at 25° C./minute
1850° C. hold for 20 hours
1850°→20° C. in 1.5 hours.

The disc was ground and polished as described in Example 1 to a thickness of 2.8±0.1 mm. The percent diffuse transmission of the disc was determined, as described in Example 1, to be 63%.

The average grain size of Sample 15 was determined in the same manner as described in Example 4. The average grain size of Sample 15 was 5.7 micrometers.

The data for sample 15 illustrate that increased soak times at 1850° C. above 10 hours have only a slight effect on the diffuse transmission and on the average grain size of a transparent $Al_2O_3$—AlMgON ceramic composite.

Various modifications and alterations of this invention will become apparent to those skilled in the art without departing from the scope and spirit of this invention, and it should be understood that this invention is not to be unduly limited to the illustrative embodiments set forth herein.

We claim:

1. A transparent ceramic article comprising $Al_2O_3$ in the range from greater than zero to less than 100 volume percent, AlMgON in the range from less than 100 to greater than zero volume percent, and porosity in the range from zero to less than 2 volume percent, based on the total volume of said article, and said article being free of transition metals and carbon in an amount sufficient to interfere with said transparency.

2. The article according to claim 1 wherein said article is colorless.

3. The article according to claim 1 wherein said AlMgON comprises in the range of 0.25 to 2 weight percent MgO, based on the total aluminum magnesium oxynitride composition.

4. The article according to claim 1 wherein said $Al_2O_3$ is present in the range of 1 to 99 volume percent and said AlMgON is present in the range of 99 to 1 volume percent, based on the total volume of said article.

5. The article according to claim 1 wherein said $Al_2O_3$ is present in the range of 45 to 65 volume percent and AlMgON is present in the range of 55 to 35 volume percent, based on the total volume of said article.

6. The article according to claim 1 wherein said porosity is in the range from more than zero to less than 2 volume percent, based on the total volume of said article.

7. The article according to claim 1 wherein said article is essentially free of porosity.

8. The article according to claim 1 which is a gas tight envelope.

9. The article according to claim 1 which is a dental device.

10. The dental device according to claim 9 wherein said device is an orthondontic bracket.

11. The article according to claim 1 which is a ferrule.

12. The article according to claim 1 wherein said article porosity is in the range from zero to less than 0.5 volume percent, based on the total volume of said article.

13. The article according to claim 1 wherein said article porosity is in the range from zero to less than 0.2 volume percent, based on the total volume of said article.

14. The article according to claim 1 wherein said AlMgON has a composition within the boundary defined by I, F, B, G, H, and E and along the boundary lines I-F, F-B, B-G, G-H, H-E, and E-I of FIG. 1 of the accompanying drawing.

15. The article according to claim 1 wherein said AlMgON has a composition within the boundary defined by J, K, L, and M and along the boundary lines J-K, K-L, L-M, and M-J of FIG. 1 of the accompanying drawing.

16. The article according to claim 1 wherein said AlMgON has a composition within the boundary defined by I, F, B, G, H, and E and along the boundary lines I-F, F-B, B-G, G-H, H-E, and E-I of FIG. 1 of the accompanying drawing.

17. The article according to claim 1 wherein said AlMgON has a composition within the boundary defined by J, K, L, and M and along the boundary lines J-K, K-L, L-M, and M-J of FIG. 1 of the accompanying drawing.

18. The article according to claim 2 wherein said AlMgON has a composition within the boundary defined by I, F, B, G, H, and E and along the boundary lines I-F, F-B, B-G, G H, H-E, and E-I of FIG. 1 of the accompanying drawing.

19. The article according to claim 2 wherein said AlMgON has a composition within the boundary defined by J, K, L, and M and along the boundary lines J-K, K-L, L-M, and M-J of FIG. 1 of the accompanying drawing.

* * * * *

UNITED STATES PATENT AND TRADEMARK OFFICE
CERTIFICATE OF CORRECTION

PATENT NO. : 5,096,862
DATED : May 17, 1992
INVENTOR(S) : James P. Mathers; Robert G. Frey It is certified that error appears in the above-identified patent and that said Letters Patent is hereby corrected as shown below:

Column 1, line 44, "Whereas" should read --whereas--.

Column 1, line 48, please delete "." after "AlN-Al$_2$O$_3$" and before "Instead."

Column 2, line 6, "Alon" should read --AlON--.

Column 2, line 49, "material" should read --materials--.

Column 4, line 17, after ";" and before "having" please add --"AlMgON" means an aluminum magnesium oxynitride--.

Column 12, line 28, "oonvection" should read --convection--.

Column 14, line 61, "(+40+50 mesh;" should read --(-40+50 mesh)--.

Column 17, line 4, "G H" should read --G-H--.

Signed and Sealed this

Nineteenth Day of October, 1993

Attest:

BRUCE LEHMAN

Attesting Officer    Commissioner of Patents and Trademarks